US008668646B2

(12) United States Patent
Stein et al.

(10) Patent No.: US 8,668,646 B2
(45) Date of Patent: *Mar. 11, 2014

(54) INTEGRATED SENSOR FOR MEDICAL APPLICATIONS (75) Inventors: Marc Stein, Chandler, AZ (US); James Ellis, Tempe, AZ (US)

(73) Assignee: Orthoseusor Inc., Dania Beach, FL (US)

(*) Notice: Subject to any disclaimer, the term of this patent is extended or adjusted under 35 U.S.C. 154(b) by 265 days.

This patent is subject to a terminal disclaimer.

(21) Appl. No.: 12/825,770

(22) Filed: Jun. 29, 2010

(65) Prior Publication Data

US 2010/0331704 A1 Dec. 30, 2010

Related U.S. Application Data (60) Provisional application No. 61/221,874, filed on Jun. 30, 2009, provisional application No. 61/221,761, filed on Jun. 30, 2009, provisional application No. 61/221,767, filed on Jun. 30, 2009, provisional application No. 61/221,779, filed on Jun. 30, 2009, provisional application No. 61/221,788, filed on Jun. 30, 2009, provisional application No. 61/221,793, filed on Jun. 30, 2009, provisional application No. 61/221,801, filed on Jun. 30, 2009, provisional application No. 61/221,808, filed on Jun. 30, 2009, provisional application No. 61/221,817, filed on Jun. 30, 2009, provisional application No. 61/221,867, filed on Jun. 30, 2009, provisional application No. 61/221,879, filed on Jun. 30, 2009, provisional application No. 61/221,881, filed on Jun. 30, 2009, provisional application No. 61/221,886, filed on Jun. 30, 2009, provisional application No. 61/221,889, filed on Jun. 30, 2009, provisional application No. 61/221,894, filed on Jun. 30, 2009, provisional application No. 61/221,901, filed on Jun. 30, 2009, provisional application No. 61/221,909, filed on Jun. 30, 2009, provisional application No. 61/221,916, filed on Jun. 30, 2009, provisional application No. 61/221,923, filed on Jun. 30, 2009, provisional application No. 61/221,929, filed on Jun. 30, 2009.

(51) Int. Cl.
*A61B 8/00* (2006.01)

(52) U.S. Cl.
USPC .............. 600/437; 600/407; 73/584; 73/596; 73/597; 73/632; 623/13.12

(58) Field of Classification Search
None
See application file for complete search history.

(56) References Cited

U.S. PATENT DOCUMENTS 4,361,154 A * 11/1982 Pratt, Jr. ..................... 600/437
4,930,511 A * 6/1990 Rossman et al. ............. 600/449

(Continued)

*Primary Examiner* — Long V. Le
*Assistant Examiner* — Bradley Impink (57) ABSTRACT A sensing assemblage (1) for capturing a transit time, phase, or frequency of energy waves propagating through a medium is disclosed to measure a parameter of the muscular-skeletal system. The sensing assemblage (1) comprises a transducer (2) and a waveguide (3). The transducer (2) is coupled to the waveguide (3) at a first location. A second transducer (11) can be coupled to the waveguide (3) at a second location. An interface material that is transmissive to acoustic energy waves can be placed between transducers (402, 404) and a waveguide (414) to improve transfer. The interface material (408, 410) can affix the transducers (402, 404) to the waveguide (414). Alternatively, a reflecting feature (5) can be placed at a second location of the waveguide (3) to reflect acoustic waves back to the transducer (2) where transducer (2) emits energy waves into the medium and detects propagated energy waves.

19 Claims, 6 Drawing Sheets

(56) References Cited

U.S. PATENT DOCUMENTS

| | | | |
|---|---|---|---|
| 4,976,267 A * | 12/1990 | Jeffcott et al. | 600/437 |
| 5,197,488 A | 3/1993 | Kovacevic | |
| 5,259,384 A * | 11/1993 | Kaufman et al. | 600/442 |
| 5,289,436 A * | 2/1994 | Terhune | 367/191 |
| 5,470,354 A | 11/1995 | Hershberger et al. | |
| 5,559,292 A * | 9/1996 | Hull et al. | 73/597 |
| 5,603,325 A * | 2/1997 | Mazess et al. | 600/442 |
| 5,651,363 A * | 7/1997 | Kaufman et al. | 600/438 |
| 5,683,396 A | 11/1997 | Tokish et al. | |
| 5,688,279 A | 11/1997 | McNulty et al. | |
| 5,871,018 A | 2/1999 | Delp et al. | |
| 5,911,159 A * | 6/1999 | Choo et al. | 73/590 |
| 6,171,252 B1 | 1/2001 | Roberts | |
| 6,245,109 B1 | 6/2001 | Mendes et al. | |
| 6,583,630 B2 | 6/2003 | Mendes et al. | |
| 6,621,278 B2 | 9/2003 | Ariav | |
| 6,701,174 B1 | 3/2004 | Krause et al. | |
| 6,714,763 B2 | 3/2004 | Hamel et al. | |
| 6,821,299 B2 | 11/2004 | Kirking et al. | |
| 6,856,141 B2 | 2/2005 | Ariav | |
| 7,001,346 B2 | 2/2006 | White | |
| 7,097,662 B2 | 8/2006 | Evans et al. | |
| 7,195,645 B2 | 3/2007 | Disilvestro et al. | |
| 7,256,695 B2 | 8/2007 | Hamel et al. | |
| 7,295,724 B2 | 11/2007 | Wang et al. | |
| 7,442,196 B2 | 10/2008 | Fisher et al. | |
| 7,575,602 B2 | 8/2009 | Amirouche et al. | |
| 7,578,821 B2 | 8/2009 | Fisher et al. | |
| 7,587,945 B2 | 9/2009 | Crottet et al. | |
| 7,615,055 B2 | 11/2009 | DiSilvestro | |
| 7,632,283 B2 | 12/2009 | Heldreth | |
| 2002/0029784 A1 | 3/2002 | Stark et al. | |
| 2005/0020941 A1 | 1/2005 | Tarabichi | |
| 2006/0058798 A1 | 3/2006 | Roman et al. | |
| 2006/0087325 A1 * | 4/2006 | Ariav et al. | 324/637 |
| 2006/0232408 A1 | 10/2006 | Nyez et al. | |
| 2006/0271112 A1 | 11/2006 | Martinson et al. | |
| 2007/0219561 A1 | 9/2007 | Lavalle et al. | |
| 2007/0272747 A1 | 11/2007 | Woods et al. | |
| 2007/0297739 A1 * | 12/2007 | Schneider et al. | 385/129 |

\* cited by examiner

INTEGRATED SENSOR FOR MEDICAL APPLICATIONS

CROSS-REFERENCE TO RELATED APPLICATIONS

This application claims the priority benefit of U.S. provisional patent applications No. 61/221,761, 61/221,767, 61/221,779, 61/221,788, 61/221,793, 61/221,801, 61/221,808, 61/221,817, 61/221,867, 61/221,874, 61/221,879, 61/221,881, 61/221,886, 61/221,889, 61/221,894, 61/221,901, 61/221,909, 61/221,916, 61/221,923, and 61/221,929 all filed 30 Jun. 2009; the disclosures of which are hereby incorporated herein by reference in their entirety.

FIELD

The present invention relates generally to measurement of physical parameters, and more particularly, real-time measurement of load, force, pressure, displacement, density, viscosity, or localized temperature by changes in the transit time of waves propagating within waveguides integrated within sensing modules or devices placed on or within a body, instrument, appliance, vehicle, equipment, or other physical system.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTIONS OF DRAWINGS

Various features of the system are set forth with particularity in the appended claims. The embodiments herein, can be understood by reference to the following description, taken in conjunction with the accompanying drawings, in which:

DETAILED DESCRIPTION

Embodiments of the invention are broadly directed to an integrated sensing device that measures applied forces, and more particularly, to sensing assemblies used therein for evaluating characteristics of energy waves propagating within waveguides. The waveguides are a conduit for guiding various kinds of waves. Changes in the compression of the waveguide are measured to evaluate changes in the applied forces. As an example, a transit time or shape of the energy wave or pulse propagating through the waveguide can be measured to determine the forces acting on the waveguide.

In all of the examples illustrated and discussed herein, any specific materials, temperatures, times, energies, etc. for process steps or specific structure implementations should be interpreted to illustrative only and non-limiting. Processes, techniques, apparatus, and materials as known by one of ordinary skill in the art may not be discussed in detail but are intended to be part of an enabling description where appropriate.

Note that similar reference numerals and letters refer to similar items in the following figures. In some cases, numbers from prior illustrations will not be placed on subsequent figures for purposes of clarity. In general, it should be assumed that structures not identified in a figure are the same as previous prior figures.

The propagation velocity of the energy waves or pulses in the waveguide is affected by physical changes of the waveguide. The physical parameter or parameters of interest can include, but are not limited to, measurement of load, force, pressure, displacement, density, viscosity, localized temperature. These parameters can be evaluated by measuring changes in the propagation time of energy pulses or waves in a waveguide relative to orientation, alignment, direction, or position as well as movement, rotation, or acceleration along an axis or combination of axes by wireless sensing modules or devices positioned on or within a body, instrument, appliance, vehicle, equipment, or other physical system.

Figure 1:
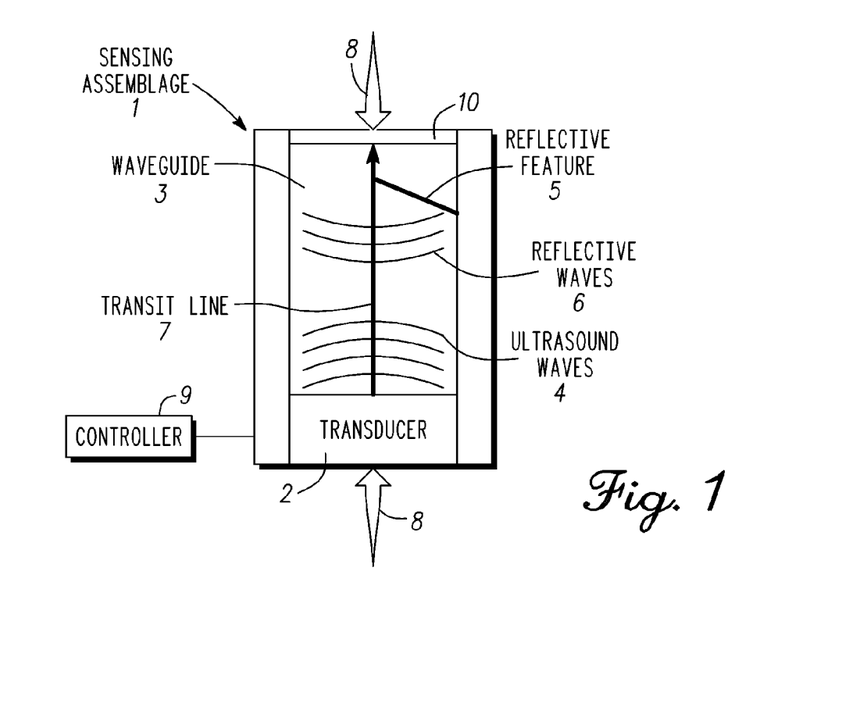
FIG. 1 is a cross-sectional view of an example sensing assemblage in accordance with one embodiment.

FIG. 1 is a side view of an example sensing assemblage 1 in accordance with one embodiment. Sensing assemblage 1 comprises an ultrasound waveguide 3 and ultrasound resonator or transducer 2, and a reflecting feature 5. The transducer 2 is coupled to waveguide 3 and can include interfacing material or materials therebetween. The interfacing material or materials promote the transfer of an acoustic signal between transducer 2 and waveguide 3. The sensing assemblage 1 enables the generation, propagation, and detection of ultrasound waves 4 within waveguide 1. In the example, the ultrasound resonator or transducer 2 and interfacing material or materials, if required, are placed in contact with, attached, or affixed to an end of waveguide 1 and ultrasound wave 4 is reflected from the opposite end of waveguide 3 or other feature or features 5 within waveguide 3. This sensing assemblage is operated in a reflectance mode. The ultrasound resonator or transducer 2 is controlled by way of controller 9 to both emit ultrasound waves 4 into waveguide 3 and detect the echo of reflected waves 6 propagating from a reflective surface 10 on one end of waveguide 3 or from reflecting feature 5. This arrangement facilitates translating changes in the length or compression of waveguide 3 due to a force 8 applied to contact surfaces into a change in the transit time 7 of ultrasound waves 4. Sensing assemblage 1 allows the translation of changes in an external parameter or parameters of interest applied to waveguide 3 into electrical signals.

Figure 8:
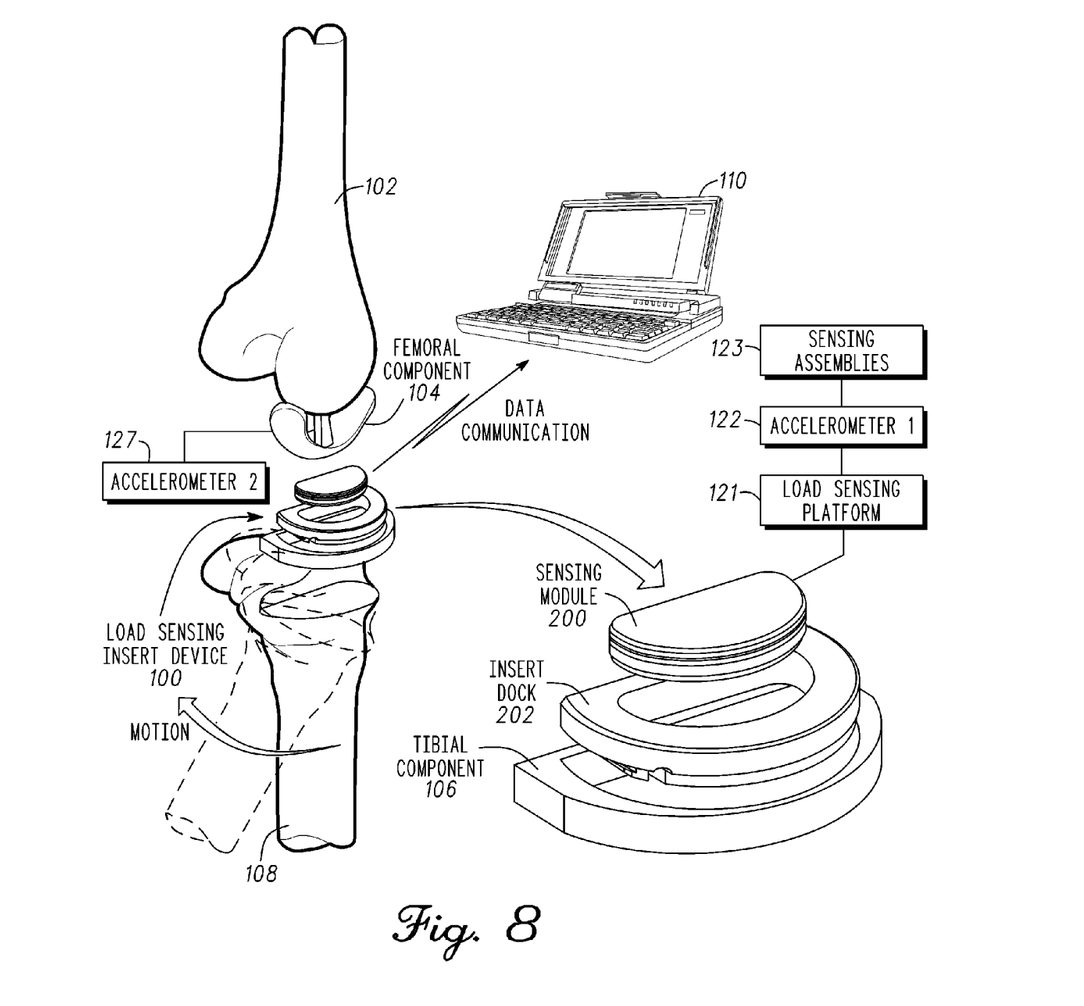
FIG. 8 is an illustration of a load sensing insert device placed in contact between a femur and a tibia for measuring a parameter in accordance with an exemplary embodiment.

The sensing assemblage 1 by way of controller 9 can measure applied forces 8. For example, briefly referring ahead, FIG. 8 shows one embodiment of a wireless sensing device 100 comprising one or more sensing assemblages. In this embodiment, the wireless sensing device by way of the sensing assemblages can assess load forces, measure a magnitude and distribution of load at various points and transmit the measured load data by way of data communication to a receiving station.

As will be explained ahead in FIG. 10, electronic assemblage within the wireless sensing device 100 integrates a power supply, sensing elements, ultrasound resonator or resonators or transducer or transducers and ultrasound waveguide waveguides, biasing spring or springs or other form of elastic members, an accelerometer, antennas and electronic circuitry that processes measurement data as well as controls all operations of ultrasound generation, propagation, and detection and wireless communications. The electronics assemblage also supports testability and calibration features that assure the quality, accuracy, and reliability of the completed wireless sensing module.

Referring back to FIG. 1, integration of components for accurately measuring the length of ultrasound waveguides includes integrating ultrasound resonators or transducers at one or both ends of an ultrasound waveguide consisting of ultrasound media. Appropriate integration of this sensing assemblage enables the flexibility to size the completed sensing assemblage from highly compact to as large as required to fit the application. The sensing assemblage may be positioned or attached or affixed, in coordination with calibrated springs or other means of elastic support, between the load bearing or contacting surfaces of a sensing module or device. In other embodiments, the ultrasound waveguide may be constructed of ultrasound media with elastic properties that eliminate the requirement for separate springs or other means of elastic structures to support the load bearing or contacting surfaces. For these embodiments of the integrated sensing assemblage, ultrasound waveguide material having the properties of deforming monotonically and linearly when compressed or stretched, and relaxing quickly without hysteresis or developing a compression or extension set are selected. In all embodiments the integrated sensing assemblage either alone, or in conjunction with springs or other means of elastic support, attached to, or positioned or affixed between, the load bearing or contact surfaces of a sensing module or device, translates load, force, pressure, density, viscosity, localized temperature, or displacement applied to the load bearing or contacting surfaces into an accurately controlled changes in the length of the ultrasound waveguide.

For applications requiring a highly compact sensing module or device, the ultrasound waveguides may be as miniaturized, but are not limited to, as lengths on the order of a millimeter. The sensing assemblage also supports submicron resolution of changes in the compression or extension of the ultrasound waveguide or waveguides over a wide range of lengths. The capability to construct highly compact sensing assemblages enables construction and operation of highly miniaturized sensing modules or devices constructed using standard components and manufacturing processes. Larger scale sensing assemblages are readily constructed using standard components and manufacturing processes.

The relationship of the propagation of ultrasound in a medium with respect to the aspect ratio of the piezoelectric element is well known. Ultrasound waves propagate linearly through the waveguide thus maintaining an accurate relationship between compression or extension and transit time of ultrasound waves. This enables accurate conversion of mechanical changes in the length or compression or extension of the waveguide into changes in the transit time of ultrasound waves or pulses within the waveguide.

Figure 2:
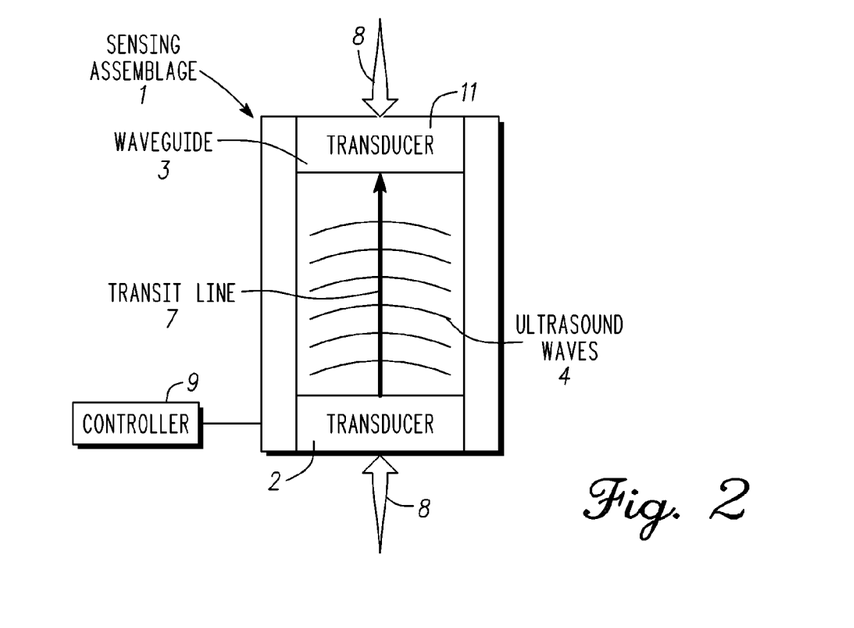
FIG. 2 is a side view of an alternate embodiment of the sensing assemblage having two transducers.

FIG. 2 is a side view of an alternate embodiment of the sensing assemblage 1 having two transducers. The illustration provides another embodiment of sensing assemblage 1 comprising ultrasound waveguide 3, ultrasound transducer 2, and an ultrasound transducer 3. Ultrasound transducers 2 and 11 are respectively coupled to a first location and second location of waveguide 3. In one embodiment, waveguide 3 is cylindrically in shape having a first and second end to which transducers are coupled. Sensing assemblage 1 supports the generation, propagation, and detection of ultrasound waves 4 within the waveguide 3. The ultrasound resonators or transducers 2 and 11 in combination with interfacing material or materials, if required, are placed in contact with, or attached or affixed to, both ends of the waveguide 3. This sensing assemblage can be operated in reflectance, unidirectional, or bi-directional modes. The arrangement facilitates translating changes in the length or compression of waveguide 3 by changes in external forces or conditions 8 into changes in the transit time 7 of ultrasound waves 4 and enabling the translation of changes in an external parameter or parameters of interest into electrical signals. The sensing assemblage by way of controller 9 can measure applied forces 8.

In general, an energy wave is directed within one or more waveguides in a device by way of continuous wave mode, pulse mode, pulse-echo mode, and pulse shaping. The waveguide 3 is a conduit that directs the energy pulse in a predetermined direction. The energy pulse is typically confined within the waveguide. In one embodiment, the waveguide comprises a polymer material. For example, urethane or polyethylene are polymers suitable for forming a waveguide. In one embodiment, the waveguide can be compressed and has little or no hysteresis in the system. The waveguide can be cylindrical in shape. A parameter applied to waveguide 3 affects a length of the waveguide 3. A relationship between the length of the waveguide 3 and the parameter is known. In a non-limiting example, the propagation time of an energy wave in waveguide 3 is measured. The length of waveguide 3 corresponds to transit time 7 and is calculated from the measurement of transit time 7. The known relationship between the length and the parameter being measured is then used to calculate the parameter value.

Figure 3:
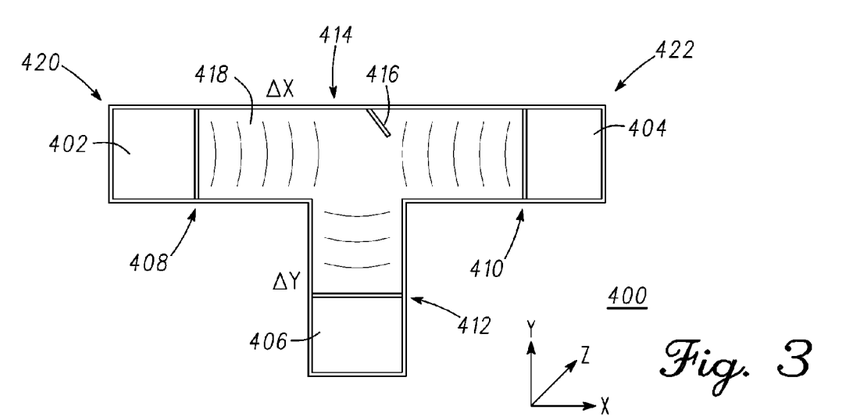
FIG. 3 is an exemplary assemblage for illustrating reflectance and unidirectional modes of operation in accordance with an exemplary embodiment.

FIG. 3 is an exemplary assemblage 400 for illustrating reflectance and unidirectional modes of operation in accordance with an exemplary embodiment. In one embodiment, assemblage 400 shows the propagation of ultrasound waves 418 within waveguide 414 in the reflectance and unidirectional modes of operation. A parameter to be measured is applied to waveguide 414. In a non-limiting example, a change in the parameter changes a dimension of the waveguide 414. A sensor system translates changes in the length or compression of waveguide 414 into changes in the transit time of ultrasound waves 418. Thus, assemblage 400 changes an external parameter or parameters of interest into electrical signals that can be further processed. Each ultrasound resonator or transducer (402, 404) in combination with interfacing material or materials (408, 410), if required, are placed in contact with, or attached or affixed to, both ends of the waveguide (420, 422). Either ultrasound resonator or transducer 402 or 404 may be selected to emit ultrasound waves, for example ultrasound resonator or transducer 402 in contact with, or attached or affixed to, one end (420) of waveguide 414, may be selected to emit ultrasound wave 418 into waveguide 414. The sensing assemblage can be operated in reflectance mode and ultrasound waves 418 may be detected by the emitting ultrasound resonator or transducer, in this example ultrasound resonator or transducer 402, after reflection from the opposite end 422 of waveguide 414 by reflecting feature, surface, interface, or body positioned at the opposite end 422 of the waveguide. In this mode, either of the ultrasound resonators or transducers 402 or 404 may be selected to emit and detect ultrasound waves.

The design of waveguide 414 supports sensing across multiple dimensions thereby permitting sensing of load forces in three-dimensions (e.g., x, y and z). By way of controller 9 (see FIG. 1) changes in length $\Delta x$ can be sensed along the waveguide propagating path formed by transducers 402 and 404 because of compression forces acting along the x-dimension. The controller 9 in view of $\Delta x$ can further sense changes in length $\Delta y$ along the waveguide propagating path formed by transducers 402 and 406 because of compression forces acting along the y-dimension. A waveguide propagating path can also be present in the z-dimension (e.g., into or out of the page) for providing sensing along the z-dimension in view of $\Delta x$ and $\Delta y$. Although the physical orientation of the propagating channels are shown at right angles (90 degrees), other embodiments can include propagating channels at different angles, for example, to measure rotation or torque.

The physical structure and orientation of the waveguide 414 in such an arrangement supports two modes of operation; reflectance mode and unidirectional mode. Unidirectional mode occurs along a direct path between a transmitter and a receiver. For instance, this occurs when transducer 402 transmits ultrasonic waves 418 along the waveguide propagating path to receiving transducer 404. In contrast, reflectance mode can occur as a result of the reflector 416 being positioned along the waveguide propagating path as shown to deflect sound waves to transducer 406 in the y-direction. The constructive design of the propagating channels in the waveguide 414 allows compression along multiple dimensions of the waveguide to permit measurements of the changes in length of the waveguide in three-dimensions. The compression occurs responsive to external load forces acting on the sensing assemblies that generates measurable compression characteristics.

In either mode, ultrasound waves 418 are generated by ultrasound resonator or transducer 402, 404, or 406 in combination with interfacing material or materials 408, 410, or 412. The ultrasound waves 418 propagate within the waveguide 414 in either reflectance mode or in unidirectional mode of operation. When operated in reflectance mode, the ultrasound waves 418 can be detected by the emitting ultrasound resonator or transducer after reflection—from the opposite end of the waveguide—by reflecting feature, surface, interface, or body at the opposite end of the waveguide thus enabling the conversion of changes in the length of compression of the waveguide 414 into electrical signals. In this mode, either of the ultrasound resonators or transducers 402, 404, or 406 may be selected to emit and detect ultrasound waves.

In unidirectional mode example, the ultrasound resonators or transducers 402 is controlled to emit ultrasound waves 418 into the waveguide 414. The other ultrasound resonator or transducer 404 is controlled to detect the ultrasound waves 418 emitted by the emitting ultrasound resonator or transducer 402. Additional reflectors 416 can be added within the waveguide 414 to reflect ultrasound waves. This can support operation in a combination of unidirectional and reflectance modes. In this mode of operation, one of the ultrasound resonators or transducers 402 is controlled to emit ultrasound waves 418 into the waveguide 414. Another ultrasound resonator or transducer 406 is controlled to detect the ultrasound waves 418 emitted by the emitting ultrasound resonator or transducer 402 subsequent to their reflection by reflector 416 thus enabling the conversion of changes in the length of compression of the waveguide 414 into electrical signals.

Figure 4:
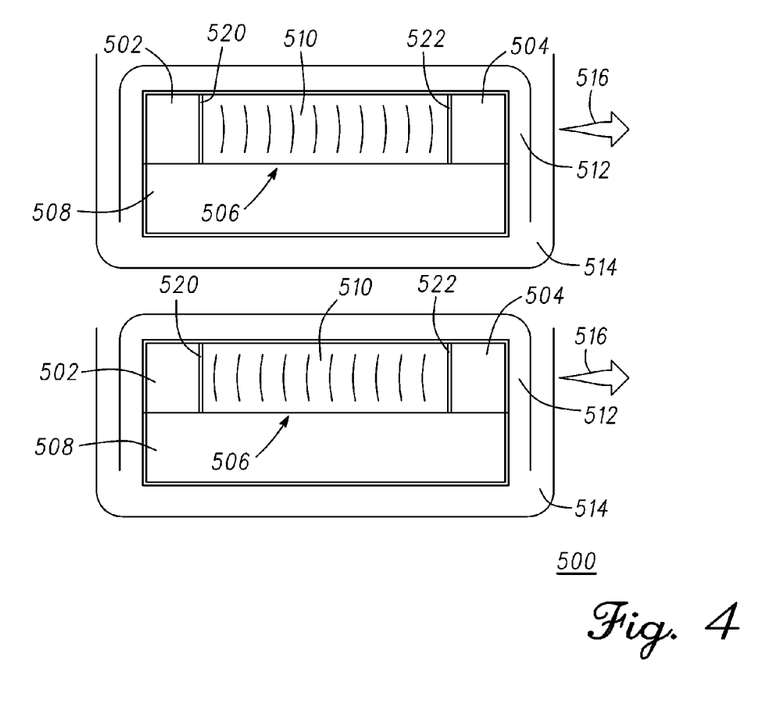
FIG. 4 is an exemplary assemblage that illustrates propagation of ultrasound waves within the waveguide in the bi-directional mode of operation of this assemblage.

FIG. 4 is an exemplary assemblage 500 that illustrates propagation of ultrasound waves 510 within the waveguide 506 in the bi-directional mode of operation of this assemblage. In this mode, the selection of the roles of the two individual ultrasound resonators or transducers (502, 504) affixed to interfacing material 520 and 522, if required, are periodically reversed. In the bi-directional mode the transit time of ultrasound waves propagating in either direction within the waveguide 506 can be measured. This can enable adjustment for Doppler effects in applications where the sensing module 508 is operating while in motion 516. Furthermore, this mode of operation helps assure accurate measurement of the applied load, force, pressure, or displacement by capturing data for computing adjustments to offset this external motion 516. An advantage is provided in situations wherein the body, instrument, appliance, vehicle, equipment, or other physical system 514, is itself operating or moving during sensing of load, pressure, or displacement. Similarly, the capability can also correct in situation where the body, instrument, appliance, vehicle, equipment, or other physical system, is causing the portion 512 of the body, instrument, appliance, vehicle, equipment, or other physical system being measured to be in motion 516 during sensing of load, force, pressure, or displacement. Other adjustments to the measurement for physical changes to system 514 are contemplated and can be compensated for in a similar fashion. For example, temperature of system 514 can be measured and a lookup table or equation having a relationship of temperature versus transit time can be used to normalize measurements. Differential measurement techniques can also be used to cancel many types of common factors as is known in the art.

In bi-directional mode ultrasonic waves 510 propagate between resonators or transducers 502 and 504 positioned at opposing ends of the ultrasound waveguide 506. This mode of operation helps assure accurate measurement of the applied load, force, pressure, displacement, density, localized temperature, or viscosity by capturing data for computing adjustments to offset this external motion. In bi-directional mode the selection of the roles of the two individual ultrasound resonators or transducers 502 and 504 with interfacing material or materials 520 and 522, if required, are periodically reversed, or intermittently scheduled, for example, under control of a processor. In this mode the transit time of ultrasound waves 510 propagating in either direction within the waveguide 506 can be measured.

The use of waveguide 506 enables the construction of low cost sensing modules and devices over a wide range of sizes, including highly compact sensing modules, disposable modules for bio-medical applications, and devices, using standard components and manufacturing processes. The flexibility to construct sensing modules and devices with very high levels of measurement accuracy, repeatability, and resolution that can scale over a wide range of sizes enables sensing modules and devices to the tailored to fit and collect data on the physical parameter or parameters of interest for a wide range of medical and non-medical applications.

Appropriate integration of this sensing assemblage enables the flexibility to size the completed sensing assemblage from highly compact to as large as required to fit the application. The sensing assemblage may be positioned or attached or affixed, in coordination with calibrated springs or other means of elastic support, between the load bearing or contacting surfaces of a sensing module or device. In other embodiments the ultrasound waveguide may be constructed of ultrasound media with elastic properties that eliminate the requirement for separate springs or other elastic structures to support the load bearing or contact surfaces of a sensing module or device. In all embodiments the integrated sensing assemblage either alone, or in conjunction with springs or other means of elastic support, attached to, or positioned or affixed between, the load bearing or contact surfaces of a sensing module or device, translates load, force, pressure, displacement, density, viscosity, or localized temperature applied to those load bearing or contacting surfaces into an accurately controlled compression, extension, or displacement of the length of the ultrasound waveguide.

For example, sensing modules or devices may be placed on or within, or attached or affixed to or within, a wide range of physical systems including, but not limited to instruments, appliances, vehicles, equipments, or other physical systems as well as animal and human bodies, for sensing the parameter or parameters of interest in real time without disturbing the operation of the body, instrument, appliance, vehicle, equipment, or physical system.

In addition to non-medical applications, examples of a wide range of potential medical applications may include, but are not limited to, implantable devices, modules within implantable devices, modules or devices within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment. Many physiological parameters within animal or human bodies may be measured including, but not limited to, loading within individual joints, bone density, movement, various parameters of interstitial fluids including, but not limited to, viscosity, pressure, and localized temperature with applications throughout the vascular, lymph, respiratory, and digestive systems, as well as within or affecting muscles, bones, joints, and soft tissue areas. For example, orthopedic applications may include, but are not limited to, load bearing prosthetic components, or provisional or trial prosthetic components for, but not limited to, surgical procedures for knees, hips, shoulders, elbows, wrists, ankles, and spines; any other orthopedic or musculoskeletal implant, or any combination of these.

Figure 5:
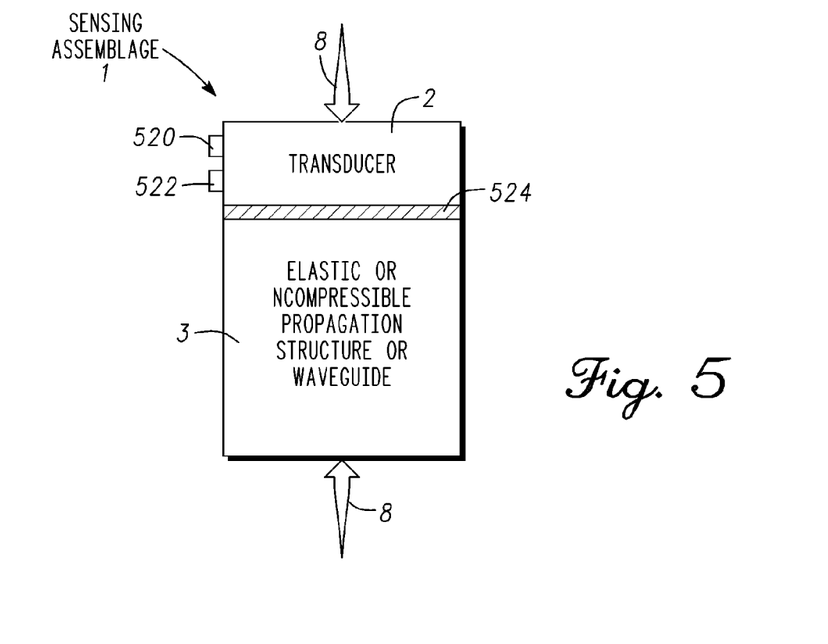
FIG. 5 illustrates in one embodiment the components of the integrated sensing assemblage.

FIG. 5 illustrates in one embodiment the components of integrated sensing assemblage 1. In one embodiment, sensing assemblage 1 includes interface material or materials 3 between ultrasound waveguide 3 and transducer 2. The interface materials 3 can aid in the transfer of acoustic energy. The ultrasound resonator or transducer 2 includes integrated electrical contacts 520 and 522 for connection with electronic driving and data capture circuitry (see FIG. 10). The ultrasound resonator or transducer 2 with interface material or materials 524, if required, is positioned in contact with, or attached or affixed to an end of ultrasound waveguide 3. In one example, interface material 3 is an adhesive that attaches transducer 2 to a surface of waveguide 3. The adhesive is a conductor of ultrasonic signals and maximizes surface area contact. Alternatively, the sensing assemblage 1 can be held under pressure such that the interfaces of waveguide 3 and transducer 2 are held under a predetermined force in contact with one another. The slight pressure maintains contact that promotes the transfer of acoustic signals at the interface but does not affect the measurement range of the sensing assemblage 1.

Figure 6:
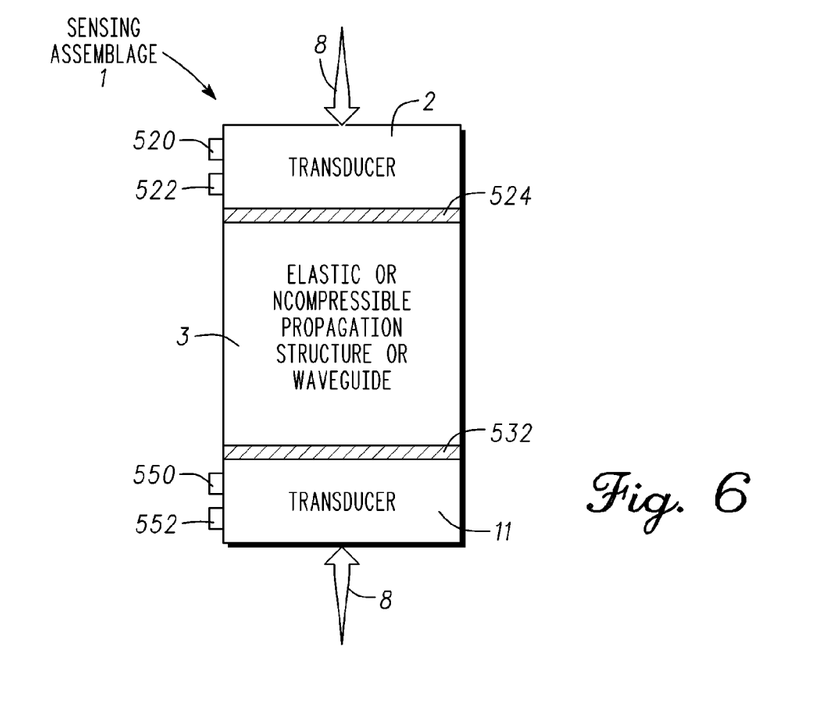
FIG. 6 illustrates the components of integrated sensing assemblage in accordance with one embodiment.

FIG. 6 illustrates the components of integrated sensing assemblage 1 in accordance with one embodiment. In one embodiment, sensing assemblage 1 comprises transducer 2, transducer 11, interfacing material 524, interfacing material 532, and waveguide 3. Transducer 2 includes contacts 520 and 522 for connection with electronic driving and data capture circuitry. Similarly, transducer 11 includes contacts 550 and 552 for connection with electronic driving and data capture circuitry. Transducer 2 is coupled to waveguide 3 at a first location. As shown, an interfacing material 524 or media is placed between transducer 2 and waveguide 3. Transducer 11 is coupled to waveguide 3 at a second location. An interfacing material 532 is placed between transducer 11 and waveguide 3. The interfacing material physically attaches to the waveguide and a corresponding transducer. The interfacing material 524 and 532 is transmissive to energy waves. In an alternate embodiment, a reflecting feature or may be added to the waveguide for more complex measurement tasks.

Figure 7:
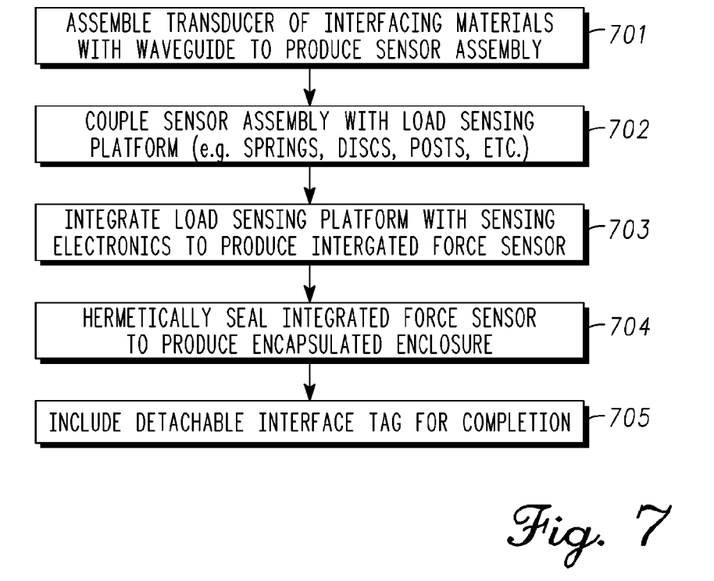
FIG. 7 is a flow chart of an exemplary method of assembling the integrated sensing assemblage.

FIG. 7 is a flow chart of an exemplary method of assembling the integrated sensing assemblage. The method 700 can include more or less than the number of steps shown, and is not limited to the order of the steps shown. For illustration purposes, with reference to FIG. 5, a single ultrasound resonator or transducer 2 with an interfacing material or materials 524 is shown. The embodiment of the integrated sensing assemblage 1 is in contact with ultrasound waveguide 3. Embodiments of the integrated sensing assemblage 1 with two ultrasound resonators or transducers as shown in FIG. 6 are assembled in the same manner.

Referring back to FIG. 7, in a step 701 transducers or interfacing materials are assembled together to produce the sensing assembly. As an example, the transducers can be affixed or connected to ends of the waveguide. An optional test as part of the method steps can then be performed on the sensing assembly to evaluate assembly integrity. In a step 702, the sensor assembly is coupled with the load sensing platform (e.g., springs, discs, posts, etc.). An optional test as part of the method steps can then be performed to evaluate coupling integrity. In a step 703, the load sensing platform can be integrated with the sensing electronics to produce an integrated force sensor. An optional test as part of the method steps can then be performed to evaluate integration. In step 704, the integrated force sensor can be hermetically sealed to produce an encapsulated enclosure. An optional test as part of the method steps can then be performed to evaluate the sealing. In a step 705, a detachable interface tag can be included to indicate completion. The tag can thereafter be removed during an insert procedure.

FIG. 8 is an illustration of a load sensing insert device 100 placed in contact between a femur 102 and a tibia 108 for measuring a parameter in accordance with an exemplary embodiment. In general, load sensing insert device 100 is placed in contact with or in proximity to the muscular-skeletal system to measure a parameter. In a non-limiting example, device 100 is used to measure a parameter of a muscular-skeletal system during a procedure such as an installation of an artificial joint. As illustrated, the device 100 in this example can intra-operatively assess a load on prosthetic components during the surgical procedure. It can collect load data for real-time viewing of the load forces over various applied loads and angles of flexion. It can measure the level and distribution of load at various points on the prosthetic component and transmit the measured load data by way data communication to a receiver station 110 for permitting visualization. This can aid the surgeon in making any adjustments needed to achieve optimal joint balancing.

The load sensing insert device 100, in one embodiment, comprises a load sensing platform 121, an accelerometer 122, and sensing assemblies 123. This permits the sensing device 100 to assess a total load on the prosthetic components when it is moving; it accounts for forces due to gravity and motion. In one embodiment, load sensing platform 121 includes two or more load bearing surfaces, at least one energy transducer, at least one compressible energy propagating structure, and at least one member for elastic support. The accelerometer 122 can measure acceleration. Acceleration can occur when the load sensing device 100 is moved or put in motion. Accelerometer 122 can sense orientation, vibration, and impact. In another embodiment, the femoral component 104 can similarly include an accelerometer 127, which by way of a communication interface to the load sensing insert device 100, can provide reference position and acceleration data to determine an exact angular relationship between the femur and tibia. The sensing assemblies 123 can reveal changes in length or compression of the energy propagating structure or structures by way of the energy transducer or transducers. Together the load sensing platform 121, accelerometer 122 (and in certain cases accelerometer 127), and sensing assemblies 123 measure force or pressure external to the load sensing platform or displacement produced by contact with the prosthetic components.

Incorporating data from the accelerometer 122 with data from the other sensing components 121 and 123 assures accurate measurement of the applied load, force, pressure, or displacement by enabling computation of adjustments to offset this external motion. This capability can be required in situations wherein the body, instrument, appliance, vehicle, equipment, or other physical system, is itself operating or moving during sensing of load, pressure, or displacement. This capability can also be required in situations wherein the body, instrument, appliance, vehicle, equipment, or other physical system, is causing the portion of the body, instrument, appliance, vehicle, equipment, or other physical system being measured to be in motion during sensing of load, pressure, or displacement.

The accelerometer 122 can operate singly, as an integrated unit with the load sensing platform 121, and/or as an integrated unit with the sensing assemblies 123. Integrating one or more accelerometers 122 within the sensing assemblages 123 to determine position, attitude, movement, or acceleration of sensing assemblages 123 enables augmentation of presentation of data to accurately identify, but not limited to, orientation or spatial distribution of load, force, pressure, displacement, density, or viscosity, or localized temperature by controlling the load and position sensing assemblages to measure the parameter or parameters of interest relative to specific orientation, alignment, direction, or position as well as movement, rotation, or acceleration along any axis or combination of axes. Measurement of the parameter or parameters of interest may also be made relative to the earth's surface and thus enable computation and presentation of spatial distributions of the measured parameter or parameters relative to this frame of reference.

In one embodiment, the accelerometer 122 includes direct current (DC) sensitivity to measure static gravitational pull with load and position sensing assemblages to enable capture of, but not limited to, distributions of load, force, pressure, displacement, movement, rotation, or acceleration by controlling the sensing assemblages to measure the parameter or parameters of interest relative to orientations with respect to the earths surface or center and thus enable computation and presentation of spatial distributions of the measured parameter or parameters relative to this frame of reference.

Embodiments of device 100 are broadly directed to measurement of physical parameters, and more particularly, to evaluating changes in the transit time of a pulsed energy wave propagating through a medium. In-situ measurements during orthopedic joint implant surgery would be of substantial benefit to verify an implant is in balance and under appropriate loading or tension. In one embodiment, the instrument is similar to and operates familiarly with other instruments currently used by surgeons. This will increase acceptance and reduce the adoption cycle for a new technology. The measurements will allow the surgeon to ensure that the implanted components are installed within predetermined ranges that maximize the working life of the joint prosthesis and reduce costly revisions. Providing quantitative measurement and assessment of the procedure using real-time data will produce results that are more consistent. A further issue is that there is little or no implant data generated from the implant surgery, post-operatively, and long term. Device 100 can provide implant status data to the orthopedic manufacturers and surgeons. Moreover, data generated by direct measurement of the implanted joint itself would greatly improve the knowledge of implanted joint operation and joint wear thereby leading to improved design and materials.

In at least one exemplary embodiment, an energy pulse is directed within one or more waveguides in device 100 by way of pulse mode operations and pulse shaping. The waveguide is a conduit that directs the energy pulse in a predetermined direction. The energy pulse is typically confined within the waveguide. In one embodiment, the waveguide comprises a polymer material. For example, urethane or polyethylene are polymers suitable for forming a waveguide. The polymer waveguide can be compressed and has little or no hysteresis in the system. In one embodiment, the waveguide is less than 10 millimeters in height. The form factor allows integration into artificial implantable components, tools, and equipment. Conversely, the muscular-skeletal system itself can be the conduit for energy waves and more specifically measured energy wave propagation. In one embodiment, the energy pulse is directed through bone of the muscular-skeletal system to measure bone density. A transit time of an energy pulse is related to the material properties of a medium through which it traverses. This relationship is used to generate accurate measurements of parameters such as distance, weight, strain, pressure, wear, vibration, viscosity, and density to name but a few.

A surgeon can affix a femoral prosthetic component 104 to the femur 102 and a tibial prosthetic component 106 to the patient's tibia 108. The tibial prosthetic component 106 can be a tray or plate affixed to a planarized proximal end of the tibia 108. The load sensing insert device 100 is fitted between the plate of the tibial prosthetic component 106 and the femoral prosthetic component 104. These three prosthetic components (104, 100 and 106) enable the prostheses to emulate the functioning of a natural knee joint. It can measure loads at various points (or locations) on the femoral prosthetic component 104 in view of the position and acceleration data and transmit the measured data to a receiving station 110. The receiving station 110 can include data processing, storage, or display, or combination thereof and provide real time graphical representation of the level and distribution of the load when the load sensing device 100 is stationary and in motion.

A proximal end of tibia 108 is prepared to receive tibial prosthetic component 106. Tibial prosthetic component 106 is a support structure that is fastened to the proximal end of the tibia and is usually made of a metal or metal alloy. The tibial prosthetic component 106 also retains the insert in a fixed position with respect to tibia 108. The insert is fitted between femoral prosthetic component 104 and tibial prosthetic component 106. The insert has at least one bearing surface that is in contact with at least condyle surface of femoral prosthetic component 104. The condyle surface can move in relation to the bearing surface of the insert such that the lower leg can rotate under load. The insert is typically made of a high wear plastic material that minimizes friction.

The condyle surface of femoral component 104 contacts a major surface of device 100. The major surface of device 100 approximates a surface of the insert. Tibial prosthetic component 106 can include a cavity or tray on the major surface that receives and retains an insert dock 202 and a sensing module 200 during a measurement process. Tibial prosthetic component 106 and device 100 have a combined thickness that represents a combined thickness of tibial prosthetic component 106 and a final (or chronic) insert of the knee joint.

In one embodiment, two devices 100 are fitted into two separate cavities, the cavities are within a trial insert (that may also be referred to as the tibial insert, rather than the tibial component itself) that is held in position by tibial component 106. One or two devices 100 may be inserted between femoral prosthetic component 104 and tibial prosthetic component 106. Each sensor is independent and each measures a respective condyle of femur 102. Separate sensors also accommodate a situation where a single condyle is repaired and only a single sensor is used. Alternatively, the electronics can be shared between two sensors to lower cost and complexity of the system. The shared electronics can multiplex between each sensor module to take measurements when appropriate. Measurements taken by device 100 aid the surgeon in modifying the absolute loading on each condyle and the balance between condyles. Although shown for a knee implant, device 100 can be used to measure other orthopedic joints such as the spine, hip, shoulder, elbow, ankle, wrist, interphalangeal joint, metatarsophalangeal joint, metacarpophalangeal joints, and others. Alternatively, device 100 can also be adapted to orthopedic tools to provide measurements.

The prosthesis incorporating device 100 emulates the function of a natural knee joint. Device 100 can measure loads or other parameters at various points throughout the range of motion. Data from device 100 is transmitted to a receiving station 110 via wired or wireless communications. In a first embodiment, device 100 is a disposable system. Device 100 can be disposed of after using the load sensing insert device 100 to optimally fit the joint implant. Device 100 is a low cost disposable system that reduces capital costs, operating costs, facilitates rapid adoption of quantitative measurement, and initiates evidentiary based orthopedic medicine. In a second embodiment, a methodology can be put in place to clean and sterilize device 100 for reuse. In a third embodiment, device 100 can be incorporated in a tool instead of being a component of the replacement joint. The tool can be disposable or be cleaned and sterilized for reuse. In a fourth embodiment, device 100 can be a permanent component of the replacement joint. Device 100 can be used to provide both short term and long term post-operative data on the implanted joint. In a fifth embodiment, device 100 can be coupled to the muscular-skeletal system. In all of the embodiments, receiving station 110 can include data processing, storage, or display, or combination thereof and provide real time graphical representation of the level and distribution of the load. Receiving station 110 can record and provide accounting information of device 100 to an appropriate authority.

In an intra-operative example, device 100 can measure forces (Fx, Fy, and Fz) with corresponding locations and torques (e.g. Tx, Ty, and Tz) on the femoral prosthetic component 104 and the tibial prosthetic component 106. The measured force and torque data is transmitted to receiving station 110 to provide real-time visualization for assisting the surgeon in identifying any adjustments needed to achieve optimal joint pressure and balancing. The data has substantial value in determining ranges of load and alignment tolerances required to minimize rework and maximize patient function and longevity of the joint.

As mentioned previously, device 100 can be used for other joint surgeries; it is not limited to knee replacement implant or implants. Moreover, device 100 is not limited to trial measurements. Device 100 can be incorporated into the final joint system to provide data post-operatively to determine if the implanted joint is functioning correctly. Early determination of a problem using device 100 can reduce catastrophic failure of the joint by bringing awareness to a problem that the patient cannot detect. The problem can often be rectified with a minimal invasive procedure at lower cost and stress to the patient. Similarly, longer term monitoring of the joint can determine wear or misalignment that if detected early can be adjusted for optimal life or replacement of a wear surface with minimal surgery thereby extending the life of the implant. In general, device 100 can be shaped such that it can be placed or engaged or affixed to or within load bearing surfaces used in many orthopedic applications (or used in any orthopedic application) related to the musculoskeletal system, joints, and tools associated therewith. Device 100 can provide information on a combination of one or more performance parameters of interest such as wear, stress, kinematics, kinetics, fixation strength, ligament balance, anatomical fit and balance.

Figure 9:
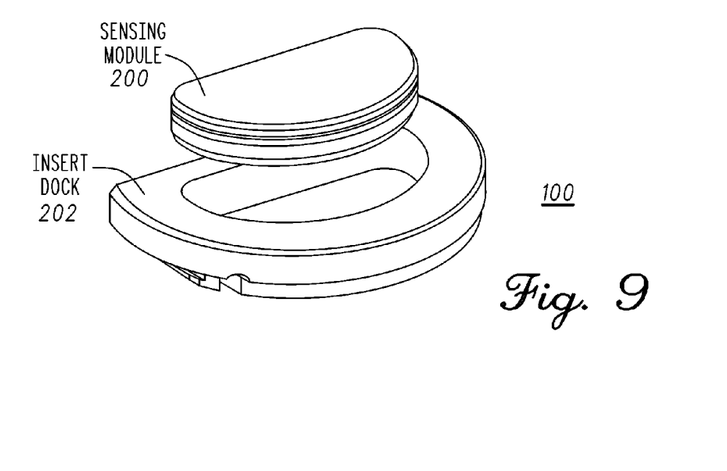
FIG. 9 is a perspective view of the medical device in accordance with one embodiment.

FIG. 9 is a perspective view of the medical device in accordance with one embodiment. As illustrated, the load sensing insert device 100 can include a sensing module 200 and an insert 202. The sensing Module 200 can securely fit within the insert dock 202. The insert dock 202 can securely attach or slide onto the tibial prosthetic component 106 (see FIG. 8). The prosthetic components of FIG. 9 can be manually coupled prior to surgical placement or during the surgery. The sensing module 200 in other embodiments (without the insert dock 202) can affix directly to load bearing surfaces exposed to forces, for example, forces applied upon a load bearing component during flexion of the joint. Although illustrated as separate, in yet another embodiment, the sensing module 200 and insert dock 202 can be combined together as an integrated sensing module.

The sensing module 200 is an encapsulating enclosure with a unitary main body and load bearing contact surfaces that can be, but are not limited to, dissimilar materials, combined to form a hermetic module or device. The components of the encapsulating enclosure may also consist of, but are not limited to, bio-compatible materials. For medical applications, the encapsulating enclosure may be required to be hermetic. The encapsulating enclosure can comprise biocompatible materials, for example, but not limited to, polycarbonate, steel, silicon, neoprene, and similar materials.

As will be discussed ahead, electronic assemblage within the sensing module 200 integrates a power supply, sensing elements, ultrasound resonator or resonators or transducer or transducers and ultrasound waveguide waveguides, biasing spring or springs or other form of elastic members, an accelerometer, antennas and electronic circuitry that processes measurement data as well as controls all operations of ultrasound generation, propagation, and detection and wireless communications. The electronics assemblage also supports testability and calibration features that assure the quality, accuracy, and reliability of the completed wireless sensing module or device. A temporary bi-directional interconnect assures a high level of electrical observability and controllability of the electronics. The test interconnect also provides a high level of electrical observability of the sensing subsystem, including the transducers, waveguides, and mechanical spring or elastic assembly. Carriers or fixtures emulate the final enclosure of the completed wireless sensing module or device during manufacturing processing thus enabling capture of accurate calibration data for the calibrated parameters of the finished wireless sensing module or device. These calibration parameters are stored within the on-board memory integrated into the electronics assemblage.

Figure 10:
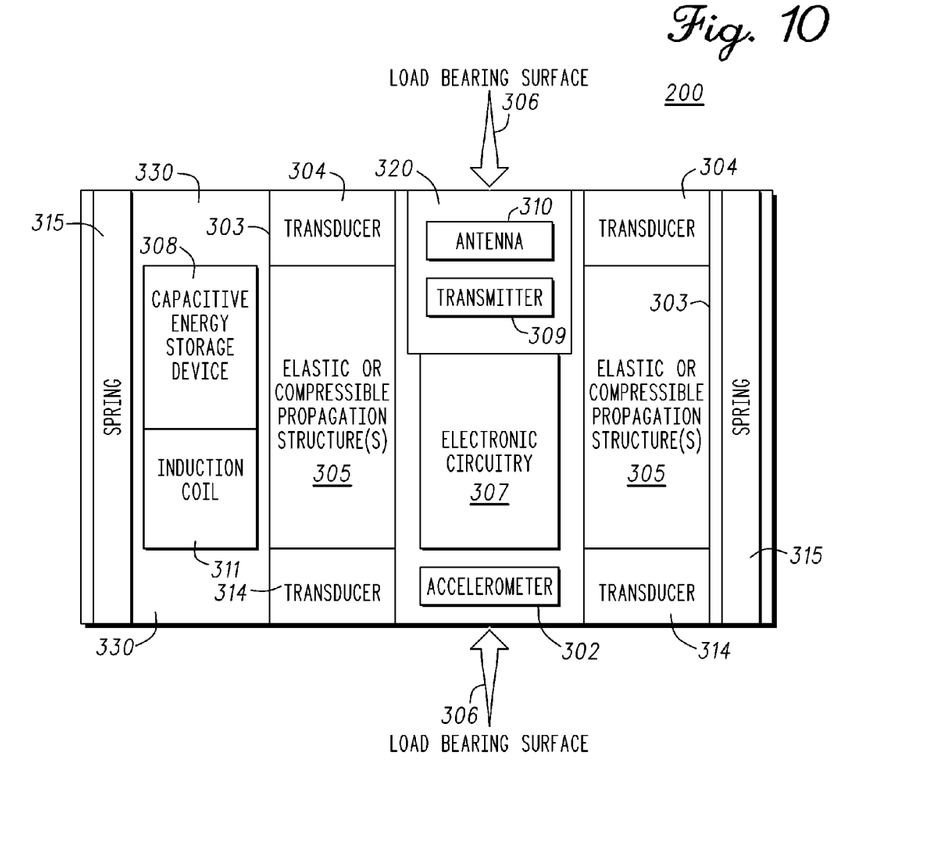
FIG. 10 is an exemplary block diagram of the components of a sensing module.

FIG. 10 is an exemplary block diagram of the components of a sensing module. It should be noted that the sensing module could comprise more or less than the number of components shown. As illustrated, the sensing module includes one or more sensing assemblages 303, a transceiver 320, an energy storage 330, electronic circuitry 307, one or more mechanical supports 315 (e.g., springs), and an accelerometer 302. In the non-limiting example, an applied compressive force can be measured by the sensing module.

The sensing assemblage 303 can be positioned, engaged, attached, or affixed to the contact surfaces 306. Mechanical supports 315 serve to provide proper balancing of contact surfaces 306. In at least one exemplary embodiment, contact surfaces 306 are load-bearing surfaces. In general, the propagation structure 305 is subject to the parameter being measured. Surfaces 306 can move and tilt with changes in applied load; actions which can be transferred to the sensing assemblages 303 and measured by the electronic circuitry 307. The electronic circuitry 307 measures physical changes in the sensing assemblage 303 to determine parameters of interest, for example a level, distribution and direction of forces acting on the contact surfaces 306. In general, the sensing module is powered by the energy storage 330.

As one example, the sensing assemblage 303 can comprise an elastic or compressible propagation structure 305 between a transducer 304 and a transducer 314. In the current example, transducer 304 can be an ultrasound (or ultrasonic) resonator, and the elastic or compressible propagation structure 305 can be an ultrasound (or ultrasonic) waveguide (or waveguides). The electronic circuitry 307 is electrically coupled to the sensing assemblages 303 and translates changes in the length (or compression or extension) of the sensing assemblages 303 to parameters of interest, such as force. It measures a change in the length of the propagation structure 305 (e.g., waveguide) responsive to an applied force and converts this change into electrical signals which can be transmitted via the transceiver 320 to convey a level and a direction of the applied force. In other arrangements herein contemplated, the sensing assemblage 303 may require only a single transducer. In yet other arrangements, the sensing assemblage 303 can include piezoelectric, capacitive, optical or temperature sensors or transducers to measure the compression or displacement. It is not limited to ultrasonic transducers and waveguides.

The accelerometer 302 can measure acceleration and static gravitational pull. Accelerometer 302 can be single-axis and multi-axis accelerometer structures that detect magnitude and direction of the acceleration as a vector quantity. Accelerometer 302 can also be used to sense orientation, vibration, impact and shock. The electronic circuitry 307 in conjunction with the accelerometer 302 and sensing assemblies 303 can measure parameters of interest (e.g., distributions of load, force, pressure, displacement, movement, rotation, torque and acceleration) relative to orientations of the sensing module with respect to a reference point. In such an arrangement, spatial distributions of the measured parameters relative to a chosen frame of reference can be computed and presented for real-time display.

The transceiver 320 comprises a transmitter 309 and an antenna 310 to permit wireless operation and telemetry functions. In various embodiments, the antenna 310 can be configured by design as an integrated loop antenna. As will be explained ahead, the integrated loop antenna is configured at various layers and locations on the electronic substrate with electrical components and by way of electronic control circuitry to conduct efficiently at low power levels. Once initiated the transceiver 320 can broadcast the parameters of interest in real-time. The telemetry data can be received and decoded with various receivers, or with a custom receiver. The wireless operation can eliminate distortion of, or limitations on, measurements caused by the potential for physical interference by, or limitations imposed by, wiring and cables connecting the sensing module with a power source or with associated data collection, storage, display equipment, and data processing equipment.

The transceiver 320 receives power from the energy storage 330 and can operate at low power over various radio frequencies by way of efficient power management schemes, for example, incorporated within the electronic circuitry 307. As one example, the transceiver 320 can transmit data at selected frequencies in a chosen mode of emission by way of the antenna 310. The selected frequencies can include, but are not limited to, ISM bands recognized in International Telecommunication Union regions 1, 2 and 3. A chosen mode of emission can be, but is not limited to, Gaussian Frequency Shift Keying, (GFSK), Amplitude Shift Keying (ASK), Phase Shift Keying (PSK), Minimum Shift Keying (MSK), Frequency Modulation (FM), Amplitude Modulation (AM), or other versions of frequency or amplitude modulation (e.g., binary, coherent, quadrature, etc.).

The antenna 310 can be integrated with components of the sensing module to provide the radio frequency transmission. The substrate for the antenna 310 and electrical connections with the electronic circuitry 307 can further include a matching network. This level of integration of the antenna and electronics enables reductions in the size and cost of wireless equipment. Potential applications may include, but are not limited to any type of short-range handheld, wearable, or other portable communication equipment where compact antennas are commonly used. This includes disposable modules or devices as well as reusable modules or devices and modules or devices for long-term use.

The energy storage 330 provides power to electronic components of the sensing module. It can be charged by wired energy transfer, short-distance wireless energy transfer or a combination thereof. External power sources can include, but are not limited to, a battery or batteries, an alternating current power supply, a radio frequency receiver, an electromagnetic induction coil, a photoelectric cell or cells, a thermocouple or thermocouples, or an ultrasound transducer or transducers. By way of the energy storage 330, the sensing module can be operated with a single charge until the internal energy is drained. It can be recharged periodically to enable continuous operation. The energy storage 330 can utilize common power management technologies such as replaceable batteries, supply regulation technologies, and charging system technologies for supplying energy to the components of the sensing module to facilitate wireless applications.

The energy storage 330 minimizes additional sources of energy radiation required to power the sensing module during measurement operations. In one embodiment, as illustrated, the energy storage 330 can include a capacitive energy storage device 308 and an induction coil 311. External source of charging power can be coupled wirelessly to the capacitive energy storage device 308 through the electromagnetic induction coil or coils 311 by way of inductive charging. The charging operation can be controlled by power management systems designed into, or with, the electronic circuitry 307. As one example, during operation of electronic circuitry 307, power can be transferred from capacitive energy storage device 308 by way of efficient step-up and step-down voltage conversion circuitry. This conserves operating power of circuit blocks at a minimum voltage level to support the required level of performance.

In one configuration, the energy storage 330 can further serve to communicate downlink data to the transceiver 320 during a recharging operation. For instance, downlink control data can be modulated onto the energy source signal and thereafter demodulated from the induction coil 311 by way of electronic control circuitry 307. This can serve as a more efficient way for receiving downlink data instead of configuring the transceiver 320 for both uplink and downlink operation. As one example, downlink data can include updated control parameters that the sensing module uses when making a measurement, such as external positional information, or for recalibration purposes, such as spring biasing. It can also be used to download a serial number or other identification data.

The electronic circuitry 307 manages and controls various operations of the components of the sensing module, such as sensing, power management, telemetry, and acceleration sensing. It can include analog circuits, digital circuits, integrated circuits, discrete components, or any combination thereof. In one arrangement, it can be partitioned among integrated circuits and discrete components to minimize power consumption without compromising performance. Partitioning functions between digital and analog circuit enhances design flexibility and facilitates minimizing power consumption without sacrificing functionality or performance. Accordingly, the electronic circuitry 307 can comprise one or more Application Specific Integrated Circuit (ASIC) chips, for example, specific to a core signal processing algorithm.

In another arrangement, the electronic circuitry can comprise a controller such as a programmable processor, a Digital Signal Processor (DSP), a microcontroller, or a microprocessor, with associated storage memory and logic. The controller can utilize computing technologies with associated storage memory such a Flash, ROM, RAM, SRAM, DRAM or other like technologies for controlling operations of the aforementioned components of the sensing module. In one arrangement, the storage memory may store one or more sets of instructions (e.g., software) embodying any one or more of the methodologies or functions described herein. The instructions may also reside, completely or at least partially, within other memory, and/or a processor during execution thereof by another processor or computer system.

Figure 11:
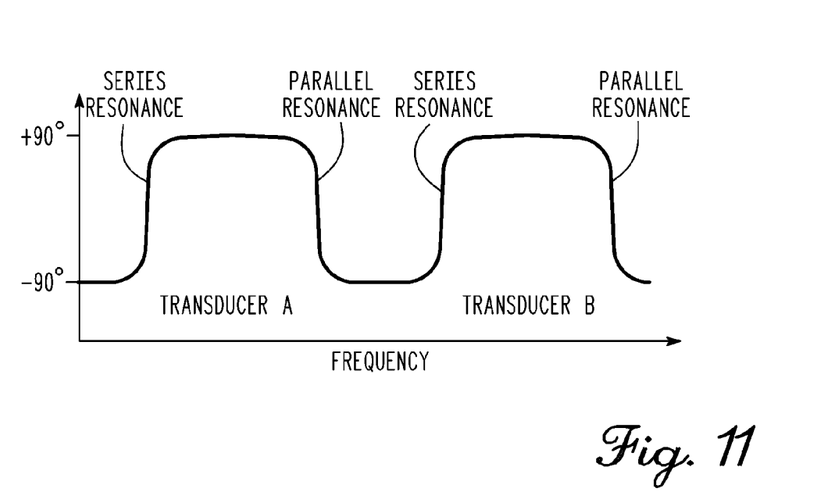
FIG. 11 is an illustration of a plot of non-overlapping resonant frequencies of paired transducers in accordance with an exemplary embodiment.

FIG. 11 is an illustration of a plot of non-overlapping resonant frequencies of paired transducers in accordance with an exemplary embodiment. In a non-limiting example, the characteristics of transducer A correspond to a first transducer driven by a transducer driver circuit as disclosed herein. The first transducer emits an energy wave into a medium at a first location. The characteristics of transducer B correspond to a second transducer for receiving a propagated energy wave. Transducer B outputs a signal corresponding to the propagated energy wave. Operation too close to their resonant frequencies results in substantial changes in phase, but limits shifts in frequency with changes in propagation through the waveguide or propagation medium. One approach to avoiding operation where the frequency of operation of an embodiment of a propagation tuned oscillator is bound this way is to select transducers with different resonant frequencies. The two transducers may be selected such that their respective series and parallel resonant frequencies do not overlap. That is, that both resonant frequencies of one transducer must be higher than either resonant frequency of the other transducer. This approach has the benefit of substantial, monotonic shifts in operating frequency of the present embodiment of a propagation tuned oscillator with changes in the transit time of energy or ultrasound waves within the waveguide or propagation medium with minimal signal processing, electrical components, and power consumption Measurement of the changes in the physical length of individual ultrasound waveguides may be made in several modes. Each assemblage of one or two ultrasound resonators or transducers combined with an ultrasound waveguide may be controlled to operate in six different modes. This includes two wave shape modes: continuous wave or pulsed waves, and three propagation modes: reflectance, unidirectional, and bi-directional propagation of the ultrasound wave. The resolution of these measurements can be further enhanced by advanced processing of the measurement data to enable optimization of the trade-offs between measurement resolution versus length of the waveguide, frequency of the ultrasound waves, and the bandwidth of the sensing and data capture operations, thus achieving an optimal operating point for a sensing module or device.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. A sensing assemblage for measuring a parameter of the muscular-skeletal system comprising:
    an ultrasound waveguide with two ends; and
    a first transducer and second transducer each placed at one of the ends of the ultrasound waveguide where the first transducer and second transducer operate together to measure changes in the propagation characteristics of ultrasound waves within the waveguide and where the sensing assemblage is configured to couple to the muscular-skeletal system;
    wherein a series and parallel resonance of the first transducer does not overlap a series and parallel resonance of the second transducer.

2. The sensing assemblage of claim 1 where the waveguide comprises urethane.

3. The sensing assemblage of claim 1 where the waveguide comprises polyethylene.

4. The sensing assemblage of claim 1 where the waveguide is elastically compressible.

5. The sensing assemblage of claim 4, where the first transducer is configured to emit a continuous wave or pulse and further including electronic circuitry operatively coupled to the second transducer where the electronic circuitry is configured to measure a change in a time of flight, differential time of flight, frequency, phase, or amplitude of the continuous wave or pulse.

6. The sensing assemblage of claim 5 where the sensing assemblage is configured to measure a force, load, or pressure.

7. The sensing assemblage of claim 6 where a relationship between waveguide length and applied force, load, or pressure is known and where the measurement of change in a time of flight, differential time of flight, frequency, phase, or amplitude of the continuous wave or pulse relates to a length of the waveguide.

8. The sensing assemblage of claim 1 where the waveguide is cylindrical in shape.

9. The sensing assemblage of claim 1, where the first transducer and the second transducer are configured to alternate between transmitting and receiving functions.

10. A sensing assemblage for measuring a parameter of the muscular-skeletal system comprising:
   a medium configured to direct ultrasonic waves;
   a first transducer coupled to the medium at a first location;
   a second transducer coupled to a medium at a second location where the first transducer and the second transducer are configure to operate together to measure changes in the propagation characteristics of ultrasound waves within the waveguide and where the first transducer and the second transducer are configured to operate such that a series and parallel resonance of the first transducer does not overlap a series and parallel resonance of the second transducer.

11. The sensing assemblage of claim 10 where the medium comprise urethane.

12. The sensing assemblage of claim 10 where the medium comprises polyethylene.

13. The sensing assemblage of claim 10 where the first or second transducer is configured to couple to bone.

14. The sensing assemblage of claim 10 where the medium comprises a prosthetic component.

15. The sensing assemblage of claim 10 where the first transducer and the second transducer are configured to measure a change in the length of the medium.

16. The sensing assemblage of claim 10 where the first transducer and the second transducer are configured to measure a change in transit time of ultrasonic waves through the medium.

17. The sensing assemblage of claim 15, where the first transducer and the second transducer by way of electronic circuitry is configured to maintain a continuous wave within the medium.

18. The sensing assemblage of claim 15, where the first transducer and the second transducer by way of electronic circuitry is configured to maintain an integer number of pulsed ultrasonic waves in the medium.

19. The sensing assemblage of claim 10, where the first transducer and the second transducer alternate between transmitting and receiving functions.

* * * * *